(12) United States Patent
Podhajsky et al.

(10) Patent No.: US 7,691,102 B2
(45) Date of Patent: Apr. 6, 2010

(54) MANIFOLD FOR GAS ENHANCED SURGICAL INSTRUMENTS

(75) Inventors: Ronald J. Podhajsky, Boulder, CO (US); Arlan J. Reschke, Longmont, CO (US)

(73) Assignee: Covidien AG, Neuhausen am Rheinfall (CH)

(*) Notice: Subject to any disclaimer, the term of this patent is extended or adjusted under 35 U.S.C. 154(b) by 971 days.

(21) Appl. No.: 11/367,724

(22) Filed: Mar. 3, 2006

(65) Prior Publication Data

US 2007/0208337 A1 Sep. 6, 2007

(51) Int. Cl.
*A61B 18/18* (2006.01)

(52) U.S. Cl. .......................................... 606/41; 606/131

(58) Field of Classification Search ............. 606/34–41, 606/45, 47–50; 607/101, 107, 113
See application file for complete search history.

(56) References Cited

U.S. PATENT DOCUMENTS

| | | | |
|---|---|---|---|
| 2,708,933 A | 5/1955 | August | |
| 2,828,747 A | 4/1958 | August | |
| 2,870,753 A * | 1/1959 | Shuck et al. | 123/25 R |
| 3,434,476 A | 3/1969 | Shaw et al. | |
| 3,569,661 A | 3/1971 | Ebeling | |
| 3,595,239 A | 7/1971 | Petersen | |
| 3,692,973 A | 9/1972 | Oku et al. | |
| 3,699,967 A | 10/1972 | Anderson | |
| 3,832,513 A | 8/1974 | Klasson | |
| 3,838,242 A | 9/1974 | Goucher | |
| 3,903,891 A | 9/1975 | Brayshaw | |
| 3,970,088 A | 7/1976 | Morrison | |
| 3,987,795 A | 10/1976 | Morrison | |
| 3,991,764 A | 11/1976 | Incropera et al. | |
| 4,014,343 A | 3/1977 | Esty | |
| 4,019,925 A | 4/1977 | Nenno et al. | |
| 4,040,426 A | 8/1977 | Morrison, Jr. | |
| 4,041,952 A | 8/1977 | Morrison, Jr. et al. | |
| 4,043,342 A | 8/1977 | Morrison, Jr. | |

(Continued)

FOREIGN PATENT DOCUMENTS

DE 3710489 11/1987

(Continued)

OTHER PUBLICATIONS

International Search Report EP 06 01 9572 dated Nov. 21, 2006.

(Continued)

*Primary Examiner*—Michael Peffley
*Assistant Examiner*—Amanda Scott

(57) ABSTRACT

There is disclosed a fluid supply manifold for use with various surgical instruments, such as, electrosurgical instruments. The fluid supply manifold includes two or more connection ports for receipt of sources of fluid supply by either bulk sources or sources contained within canisters. The manifold may include a mixing chamber for mixing the various sources of fluids within the manifold or may include flow tubes for providing the sources of fluid directly to the surgical instrument to be mixed within the surgical instrument. Control valves are associated with each of the connection ports to control the flow of fluids through the manifold. The manifold may also include a gas inlet to facilitate drawing the fluids out of the various sources as well as mixing the fluids within the manifold.

12 Claims, 9 Drawing Sheets

U.S. PATENT DOCUMENTS

| | | | |
|---|---|---|---|
| 4,057,064 A | 11/1977 | Morrison, Jr. et al. | |
| 4,060,088 A | 11/1977 | Morrison, Jr. et al. | |
| 4,209,018 A | 6/1980 | Meinke et al. | |
| 4,242,562 A | 12/1980 | Karinsky et al. | |
| 4,311,145 A | 1/1982 | Esty et al. | |
| 4,492,231 A | 1/1985 | Auth | |
| 4,492,845 A | 1/1985 | Kljuchko et al. | |
| 4,545,375 A | 10/1985 | Cline | |
| 4,577,637 A | 3/1986 | Mueller, Jr. | |
| 4,601,701 A | 7/1986 | Mueller, Jr. | |
| 4,665,906 A | 5/1987 | Jervis | |
| 4,708,137 A | 11/1987 | Tsukagoshi | |
| 4,711,238 A | 12/1987 | Cunningham | |
| 4,728,322 A | 3/1988 | Walker et al. | |
| 4,732,556 A | 3/1988 | Chang et al. | |
| 4,753,223 A | 6/1988 | Bremer | |
| 4,781,175 A * | 11/1988 | McGreevy et al. | 606/40 |
| 4,817,613 A | 4/1989 | Jaraczewski et al. | |
| 4,822,557 A | 4/1989 | Suzuki et al. | |
| 4,864,824 A | 9/1989 | Gabriel et al. | |
| 4,890,610 A | 1/1990 | Kirwan, Sr. et al. | |
| 4,901,719 A | 2/1990 | Trenconsky et al. | |
| 4,901,720 A | 2/1990 | Bertrand | |
| 4,931,047 A | 6/1990 | Broadwin et al. | |
| 4,955,863 A | 9/1990 | Walker et al. | |
| 5,015,227 A | 5/1991 | Broadwin et al. | |
| 5,041,110 A | 8/1991 | Fleenor | |
| 5,061,268 A | 10/1991 | Fleenor | |
| 5,061,768 A | 10/1991 | Kishimoto et al. | |
| 5,067,957 A | 11/1991 | Jervis | |
| 5,088,997 A | 2/1992 | Delahuerga et al. | |
| 5,098,430 A | 3/1992 | Fleenor | |
| 5,108,389 A | 4/1992 | Cosmescu | |
| RE33,925 E | 5/1992 | Bales et al. | |
| 5,122,138 A | 6/1992 | Manwaring | |
| D330,253 S | 10/1992 | Burek | |
| 5,152,762 A | 10/1992 | McElhenney | |
| 5,160,334 A | 11/1992 | Billings et al. | |
| 5,163,935 A | 11/1992 | Black et al. | |
| 5,195,959 A | 3/1993 | Smith | |
| 5,195,968 A | 3/1993 | Lundquist et al. | |
| 5,207,675 A | 5/1993 | Canady | |
| 5,217,457 A | 6/1993 | Delahuerga et al. | |
| 5,234,457 A | 8/1993 | Andersen | |
| 5,242,438 A | 9/1993 | Saadatmonesh et al. | |
| 5,244,462 A | 9/1993 | Delahuerga et al. | |
| 5,248,311 A | 9/1993 | Black et al. | |
| 5,256,138 A | 10/1993 | Burek et al. | |
| RE34,432 E | 11/1993 | Bertrand | |
| 5,292,320 A | 3/1994 | Brown et al. | |
| 5,306,238 A | 4/1994 | Fleenor | |
| 5,324,283 A | 6/1994 | Heckele | |
| 5,330,469 A * | 7/1994 | Fleenor | 606/40 |
| RE34,780 E | 11/1994 | Trenconsky et al. | |
| 5,366,456 A | 11/1994 | Rink et al. | |
| 5,370,649 A | 12/1994 | Gardetto et al. | |
| 5,380,317 A | 1/1995 | Everett et al. | |
| 5,389,390 A | 2/1995 | Kross | |
| 5,476,461 A | 12/1995 | Cho et al. | |
| 5,496,308 A | 3/1996 | Brown et al. | |
| 5,537,499 A | 7/1996 | Brekke | |
| 5,620,439 A | 4/1997 | Abela et al. | |
| 5,653,689 A | 8/1997 | Buelna et al. | |
| 5,662,621 A | 9/1997 | Lafontaine | |
| 5,669,904 A | 9/1997 | Platt, Jr. et al. | |
| 5,669,907 A | 9/1997 | Platt, Jr. et al. | |
| 5,688,261 A | 11/1997 | Amirkhanion et al. | |
| 5,700,260 A | 12/1997 | Cho et al. | |
| 5,716,365 A | 2/1998 | Goicoechea et al. | |
| 5,720,745 A | 2/1998 | Farin et al. | |
| 5,782,860 A | 7/1998 | Epstein et al. | |
| 5,782,896 A | 7/1998 | Chen et al. | |
| 5,797,920 A | 8/1998 | Kim | |
| 5,800,500 A | 9/1998 | Spelman et al. | |
| 5,800,516 A | 9/1998 | Fine et al. | |
| 5,821,664 A | 10/1998 | Shahinpoor | |
| 5,836,944 A | 11/1998 | Cosmescu | |
| 5,848,986 A | 12/1998 | Lundquist et al. | |
| 5,855,475 A | 1/1999 | Fujio et al. | |
| 5,908,402 A | 6/1999 | Blythe | |
| 5,964,714 A | 10/1999 | Lafontaine | |
| 5,964,752 A * | 10/1999 | Stone | 606/27 |
| 5,972,416 A | 10/1999 | Reimels et al. | |
| 6,039,736 A | 3/2000 | Platt | |
| 6,080,183 A | 6/2000 | Tsugita et al. | |
| 6,102,940 A | 8/2000 | Robichon et al. | |
| 6,117,167 A | 9/2000 | Goicoechea et al. | |
| 6,139,519 A | 10/2000 | Blythe | |
| 6,149,648 A | 11/2000 | Cosmescu | |
| 6,162,232 A * | 12/2000 | Shadduck | 606/131 |
| 6,197,026 B1 | 3/2001 | Farin et al. | |
| 6,206,878 B1 * | 3/2001 | Bishop et al. | 606/49 |
| 6,213,999 B1 | 4/2001 | Platt, Jr. et al. | |
| 6,264,650 B1 | 7/2001 | Hovda et al. | |
| 6,277,115 B1 * | 8/2001 | Saadat | 606/41 |
| 6,348,051 B1 | 2/2002 | Farin et al. | |
| 6,458,125 B1 | 10/2002 | Cosmescu | |
| 6,475,217 B1 | 11/2002 | Platt | |
| 6,558,383 B2 | 5/2003 | Cunningham et al. | |
| 6,579,288 B1 * | 6/2003 | Swanson et al. | 606/41 |
| 6,602,249 B1 | 8/2003 | Stoddard | |
| 6,616,660 B1 | 9/2003 | Platt | |
| 6,666,865 B2 | 12/2003 | Platt | |
| 6,702,810 B2 * | 3/2004 | McClurken et al. | 606/34 |
| 6,852,112 B2 | 2/2005 | Platt | |
| 6,883,517 B2 * | 4/2005 | Halamish | 128/200.18 |
| 6,911,029 B2 | 6/2005 | Platt | |
| 6,942,661 B2 * | 9/2005 | Swanson | 606/41 |
| 7,033,353 B2 | 4/2006 | Stoddard | |
| 2001/0018587 A1 | 8/2001 | Yamamoto | |
| 2002/0022838 A1 | 2/2002 | Cunningham et al. | |
| 2003/0093073 A1 | 5/2003 | Platt | |
| 2003/0144654 A1 | 7/2003 | Hilal | |
| 2004/0088029 A1 | 5/2004 | Yamamoto | |
| 2004/0167512 A1 | 8/2004 | Stoddard | |
| 2005/0004565 A1 * | 1/2005 | Vanney | 606/41 |
| 2005/0015086 A1 | 1/2005 | Platt | |
| 2005/0033278 A1 * | 2/2005 | McClurken et al. | 606/41 |
| 2005/0070894 A1 | 3/2005 | McClurken | |
| 2005/0171528 A1 * | 8/2005 | Sartor et al. | 606/41 |
| 2005/0197658 A1 | 9/2005 | Platt | |
| 2006/0052771 A1 | 3/2006 | Sartor | |

FOREIGN PATENT DOCUMENTS

| | | |
|---|---|---|
| DE | 4139029 | 6/1993 |
| DE | 4326037 | 2/1995 |
| DE | 9117019 | 4/1995 |
| DE | 195 37 897 | 3/1997 |
| DE | 9117299 | 4/2000 |
| DE | 19848784 | 5/2000 |
| DE | 29724247 | 8/2000 |
| EP | 0 447 121 A2 | 9/1991 |
| EP | 0 612 535 | 8/1994 |
| EP | 956827 | 11/1999 |
| EP | 1 090 599 | 4/2001 |
| EP | 1 127 551 A1 | 8/2001 |
| EP | 1 561 430 A1 | 8/2005 |
| EP | 1561430 | 8/2005 |
| EP | 1 570 798 A2 | 9/2005 |
| EP | 1 595 507 A2 | 11/2005 |
| FR | 1340509 | 9/1963 |
| GB | L014995 | 12/1965 |
| JP | 61-159953 | 7/1986 |

| | | |
|---|---|---|
| SU | 1438745 | 11/1988 |
| WO | WO91/13593 | 9/1991 |
| WO | WO93/03678 | 3/1993 |
| WO | WO 96/24301 | 8/1996 |
| WO | WO96/27337 | 9/1996 |
| WO | WO99/015091 | 4/1999 |
| WO | WO 01/62333 | 8/2001 |
| WO | WO 02/058762 | 8/2002 |
| WO | WO 2005/016142 | 2/2005 |

OTHER PUBLICATIONS

European Search Report.
Grund et al., "Endoscopic Argon Plasma . . . Flexible Endoscopy" Surgery and Allied Technologies, No. 1, vol. 2, pp. 42-46 (Feb. 1994).
Farin et al., "Technology of Argon Plasma . . . Endoscopic Applications" Endoscopic Surgery and Allied Technologies, No. 1, vol. 2, pp. 71-77 (Feb. 1994).
Brand et al., "Electrosurgical Debulking of Ovarian Cancer: A New Technique Using the Argon Beam Coagulator" Gynecologic Oncology 39 pp. 115-118 (1990).
Hemandez et al., "A Controlled Study of the Argon Beam Coagultor for Partial Nephrectomy" The Journal of Urology, vol. 143, May (J. Urol. 143: pp. 1062-1065, 1990).
Ward et al., "A Significant New Contribution to Radical Head and Neck Surgery" Arch Otolaryngology, Head and Neck Surg., vol. 115 pp. 921-923 (Aug. 1989).
Mark H. Mellow, "The Role of Endoscopic Laser Therapy in Gastrointestinal Neoplasms" Advanced Therapeutic Endoscopy, pp. 17-21.
Silverstein et al., "Thermal Coagulation Therapy for Upper Gatrointestinal Bleeding" Advanced Therapeutic Endoscopy, pp. 79-84.
Way et al., "Techniques in Therapeutic Endoscopy" W.B. Saunders Company, Philadelphia, PA., pp. 1.7-1.15.
International Search Report 01102843.8-2305.
International Search Report PCT/US98/19284.
European Searh Report EP 05 00 2257.
Extended European Search Report for European Patent Application No. EP 07 00 4356 dated Jul. 2, 2007 (7 pages).

* cited by examiner

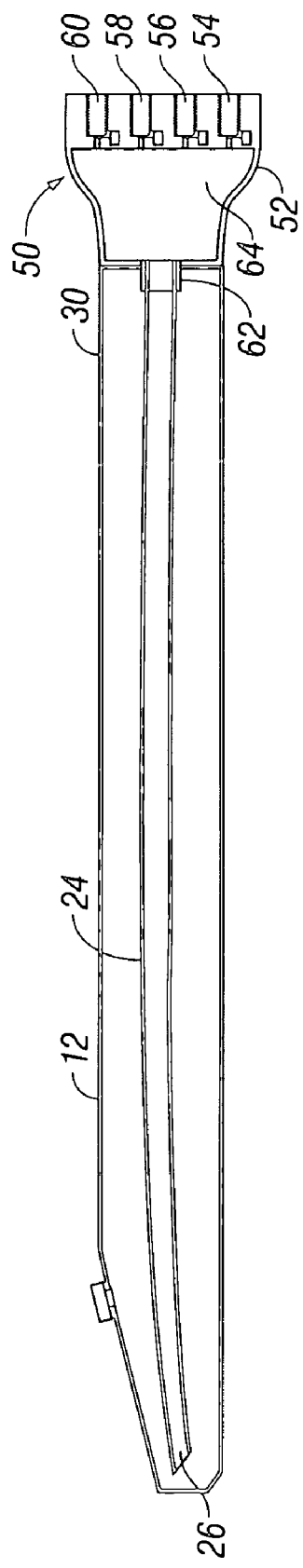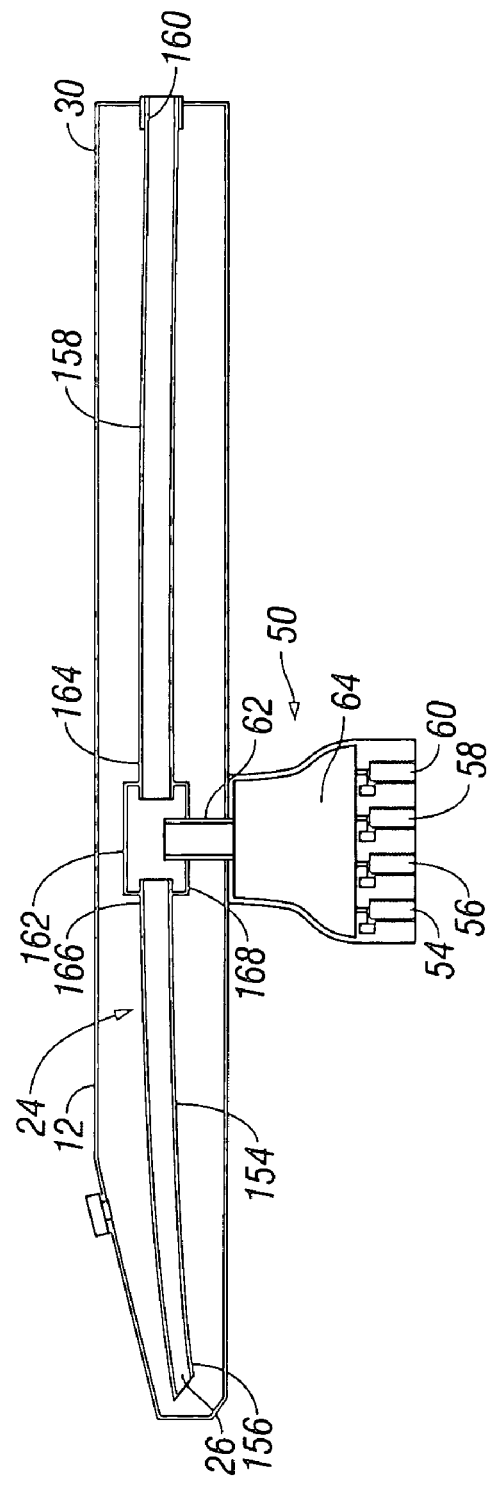
FIG. 8
FIG. 9

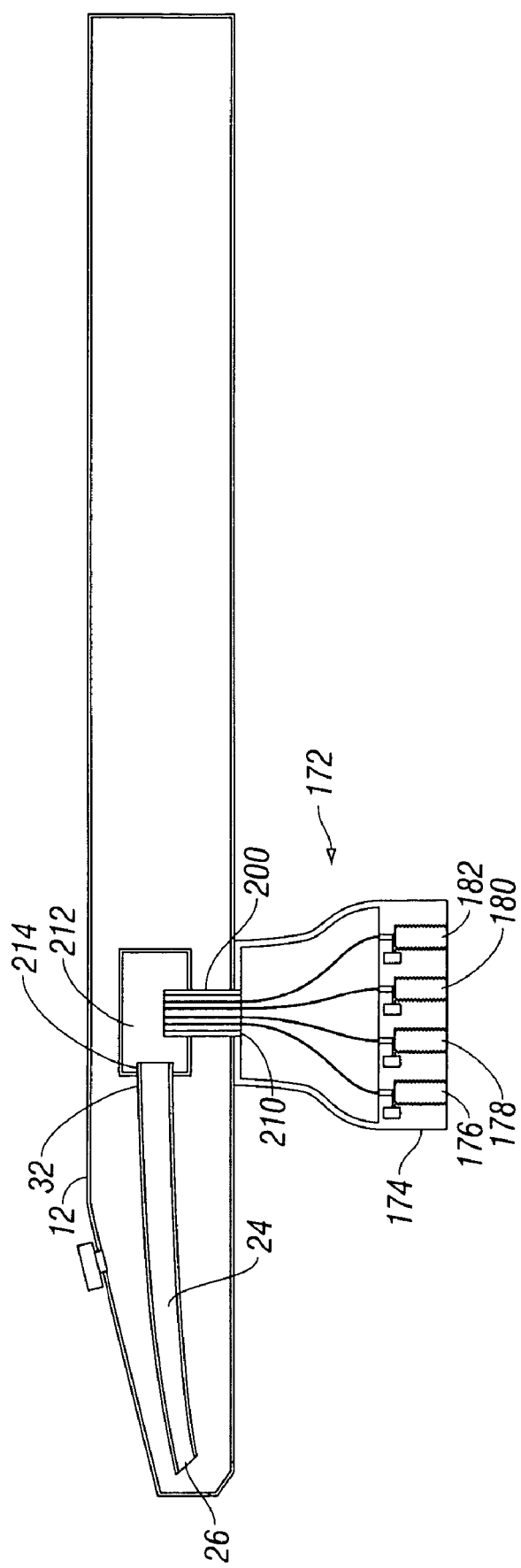

MANIFOLD FOR GAS ENHANCED SURGICAL INSTRUMENTS

BACKGROUND

1. Technical Field

The present disclosure relates generally to gas enhanced electrosurgical instruments. More particularly, the present disclosure relates to a supply manifold for use with a gas enhanced electrosurgical instrument having multiple material supply cylinders.

2. Background of Related Art

Various surgical instruments are known for treating tissue. For example, surgical instruments used for tissue division, dissection, ablation, or for arresting blood loss and coagulation are well-known. In a particular application, for example in a coagulation instrument, an electrode is used in conjunction with a heated probe to arrest bleeding.

Some prior art devices include a tube-like coagulation instrument in which an ionizable gas is supplied to the instrument and ionized by the electrode. The provision of an atmosphere of ionized gases is beneficial because it helps focus the energy adjacent the electrode and it displaces oxygen from the area and reduces oxidative stress of the tissue. The gas is propelled from the instrument toward the tissue.

Many surgical procedures are enhanced by the use of wound mediating substances to assist in the healing of tissue. The substances may include blood clotting factors, wound closing adhesives, growth factors, interleukins, cytokines, inflammatory mediating factors, chemokines, meta-metalloproteinase or other biochemicals known to mediate wound healing.

In certain surgeries it may be advantageous to provide other fluids, such as, for example, saline, various dyes, etc. to the surgical instrument for application to tissue. In some instances, it may be advisable to provide one or more of these fluids to the tissue at the same time.

SUMMARY

The present disclosure relates to a fluid supply manifold for use with a surgical instrument to provide various fluids from balk or canister fluid supply sources to the surgical instrument. The fluid supply manifold generally includes a housing having at least two connection ports for receipt of sources of fluid supply. A flow port is provided on each of the connection ports to pass the fluid through the housing. In one embodiment, the housing defines a mixing chamber that is in fluid communication with each of the flow ports so as to mix the fluids supplied through the connection ports. The housing also includes a discharge tube that is in fluid communication with the mixing chamber. Control valves are associated with the connection ports to regulate the flow of fluid into the housing. The control valves are operated by an actuator associated with a surgical instrument assembly. The housing may also include a gas inlet port that is in fluid communication with the mixing chamber.

Needles, defining fluid flow paths, are associated with the connection ports for piercing a septum associated with various fluid supply sources. The fluid supply sources may include bulk sources or individual fluid supply canisters. The connection ports include O-rings for sealing engagement with the fluid supply sources. In one embodiment, the connection ports are threaded to receive a corresponding thread on a fluid supply source. In an alternative embodiment, the external fluid supply source is affixed within the connection port in a press fit fashion such that the needle is forced through a septum of the fluid supply source.

In an alternative embodiment of the manifold, each connection port includes a flow tube passing through the housing. Control valves are positioned between a flow port of the connection port and the flow tubes. The flow tubes exit the housing through a neck, which is also used to connect the manifold to a surgical instrument or an actuator assembly.

The present disclosure also relates to a surgical instrument assembly including a surgical instrument having a fluid flow tube that includes a discharge port at a distal end of the surgical instrument. The surgical instrument assembly also includes an actuator assembly for controlling the flow of fluids through the fluid flow tube as well as a manifold supplying at least one or more sources of fluid to the fluid flow tube. In one embodiment, the manifold is attached to the actuator of the actuator assembly. In an alternative embodiment, the manifold is attached to the surgical instrument. The manifold can be attached to a proximal end of the surgical instrument or can be attached to a mixing chamber associated with the surgical instrument.

The present disclosure also relates to a gas enhanced electrosurgical instrument assembly that includes an electrosurgical instrument having a fluid flow tube including a fluid discharge port at a distal end of the surgical instrument. The instrument assembly also includes a generator for providing a source of energy to the electrosurgical instrument and a manifold for supplying one or more sources to the fluid flow tube of the electrosurgical instrument. An actuator assembly, having an actuator, is provided for controlling the source of energy provided by the generator and the flow of fluids from the manifold to the fluid flow tube of the electrosurgical instrument assembly. In one embodiment, the manifold is affixed to the actuator assembly. In an alternative embodiment, the manifold is affixed to the electrosurgical instrument.

DESCRIPTION OF THE DRAWINGS

Various embodiments of the presently disclosed supply manifold for use with a gas enhanced electrosurgical instrument are disclosed herein with reference to the drawings, wherein.

FIG. 8 is a side partial sectional view of one embodiment of a gas enhanced electrosurgical instrument with a supply manifold mounted thereon;

FIG. 9 is a side view, partially shown in section, of an alternate embodiment of a gas enhanced electrosurgical instrument with a supply manifold mounted thereon;

FIG. 15 is a side view, partially shown in section, of a further embodiment of a gas enhanced electrosurgical instrument with the supply manifold of FIG. 12 mounted thereon.

DETAILED DESCRIPTION

Embodiments of the presently disclosed manifolds for use with gas enhanced instruments will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
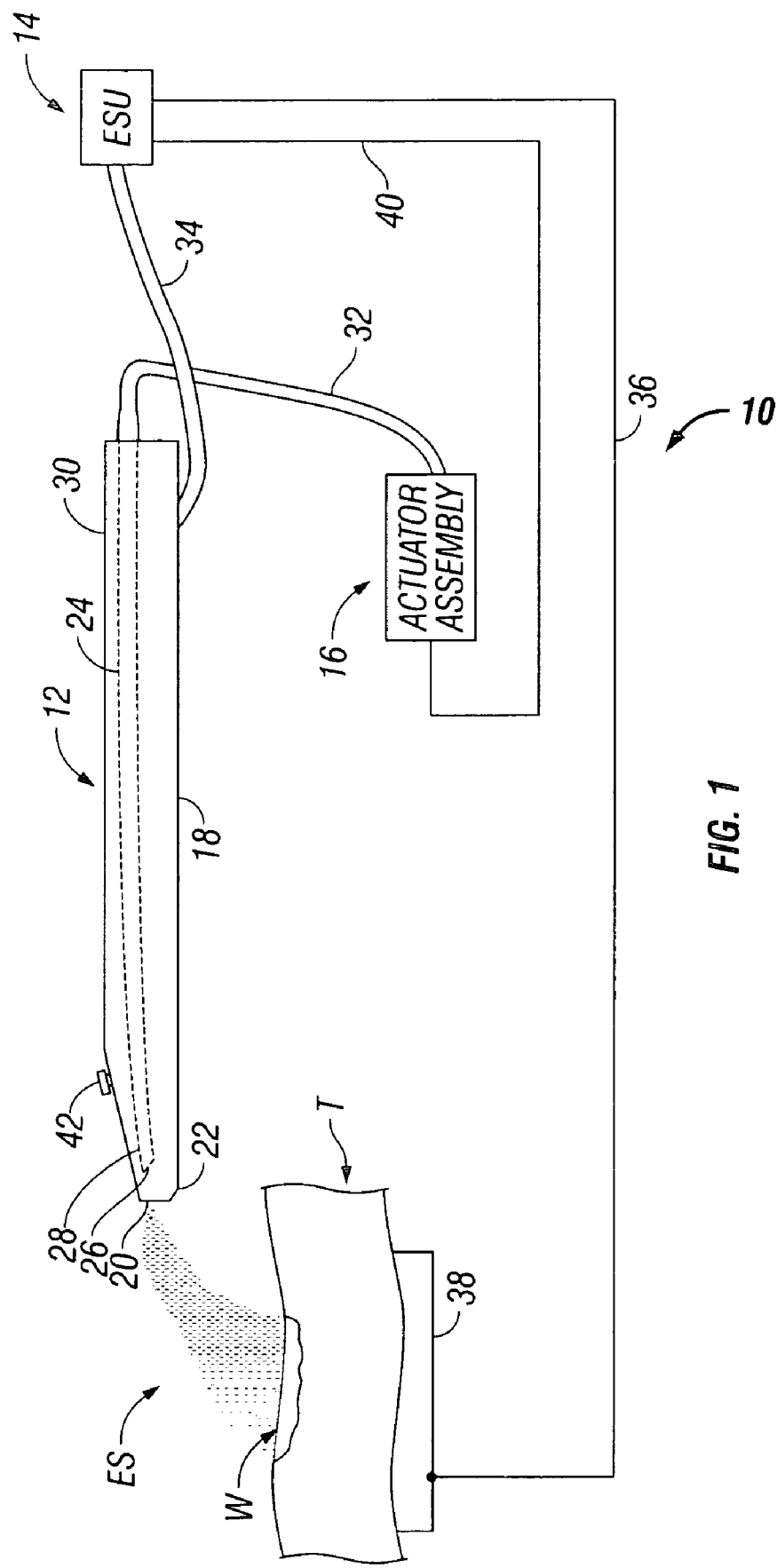
FIG. 1 is a schematic view of a gas enhanced electrosurgical instrument system.

Referring initially to FIG. 1, there is disclosed a gas enhanced electrosurgical instrument assembly or instrument assembly 10 of the type disclosed in U.S. patent application Ser. No. 11/229,779 entitled "GAS-ENHANCED SURGICAL INSTRUMENT WITH PRESSURE SAFETY FEATURE" the entire disclosure of which is incorporated by reference herein. Instrument assembly 10 is used to cut or coagulate tissue during various surgical procedures. Instrument assembly 10 generally includes an electrosurgical instrument 12, an energy generator 14 and an actuator 16. Energy generator 14 provides a source of energy for electrosurgical instrument 12 and actuator assembly 16 controls the flow of energy to electrosurgical instrument 12 as well as controls the flow of a gas, such as, for example, argon gas through electrosurgical instrument 12 to facilitate application of the energy provided by energy generator 14 to a wound W in a tissue T.

Electrosurgical instrument 12 generally includes a housing 18 having an opening 20 at a distal end 22 thereof. The energy provided by energy generator 14 ionizes the gas supplied by actuator assembly 16 such that the ionized gas is propelled out of opening 20 to form an energy stream ES as electrosurgical instrument 12 is used to apply energy to tissue. A flow tube 24 extends between actuator 16 and distal end 22 of housing 18 to conduct the flow of fluids between actuator assembly 16 and electrosurgical instrument 12. Flow tube 24 has a fluid discharge port 26 at a distal end 28 of flow tube 24 which is positioned adjacent opening 20 electrosurgical instrument 12. While not specifically shown, an electrode is provided within electrosurgical instrument adjacent opening 20 so as to ionize the gas flowing through opening 20 and facilitate application of energy to tissue T. Flow tube 24 extends through a proximal end 30 electrosurgical instrument 12 such that a proximal end 32 of flow tube 24 is connected to actuator assembly 16. In this disclosed embodiment, the source of gas may be entirely contained within actuator assembly 16 or may be provided by an external source routed through actuator assembly 16. Additionally, the source of gas may be provided from a manifold associated with actuator assembly 16 or directly with electrosurgical instrument 12 in a manner described in more detail hereinbelow.

Generator 14 is of the type used to provide sources of energy, such as RF energy, to various electrosurgical instruments for use in cutting or coagulating tissue. Particularly useful generators 14 are the types available from Valley-Lab—a division of Tyco Healthcare Group LP. Generator 14 is connected to electrosurgical instrument 12 by an energy cable 34. An energy return path 36 extends between generator 14 and a return pad 38. In use, return pad 38 is typically affixed to a portion of a patient to provide a complete flow of energy from generator 14 through electrosurgical instrument 12 to cut or coagulate tissue at a wound W, passed through underlying tissue T and into return pad 38 and thus back through return path 36 to generator 14. A control wire 40 extends between actuator 16 and generator 14 such that the energy provided by generator 14 to electrosurgical instrument 12 is controlled by actuator assembly 16. In some applications, a pressure relief valve 42 may be provided on electrosurgical instrument 10 to purge any built up fluid pressure within flow tube 24 prior to or during surgery.

Figure 2:
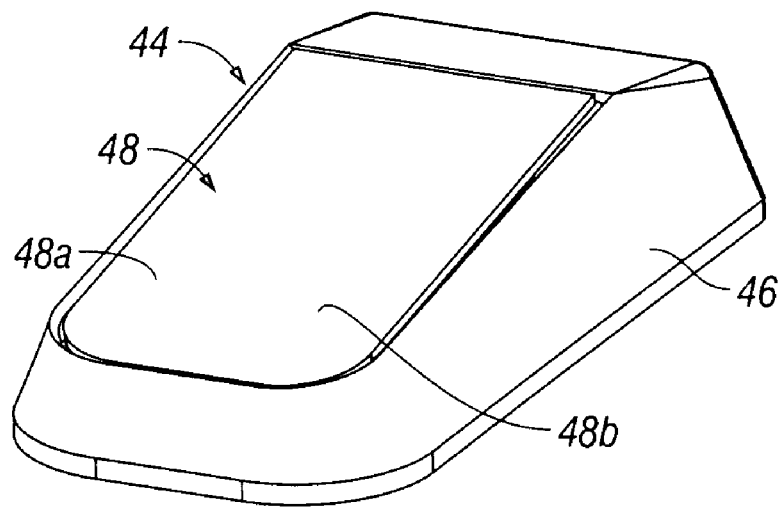
FIG. 2 is a perspective view of an actuator for use with a gas enhanced electrosurgical instrument.

Referring now to FIG. 2, a particular embodiment of actuator assembly 16 may be provided in the form of a foot-operated actuator 44. Actuator 44 generally includes a housing 46 having a foot switch 48 for controlling the flow of energy from generator 14, as well as, the flow of gas from actuator assembly 16. Foot switch 48 may be divided into several different control pedals, such as, for example, control pedals 48a and 48b. While actuator 44 is illustrated with only two control pedals 48a and 48b, depending upon the number of operations, or substances to be controlled, more than two control pedals may be provided on actuator 44.

Figure 3:
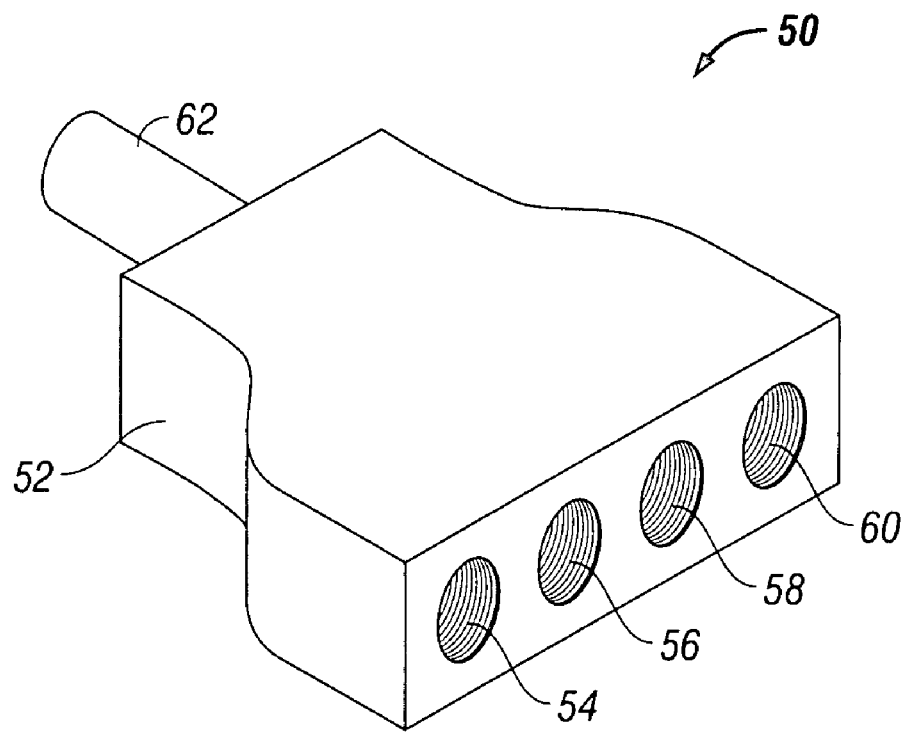
FIG. 3 is a perspective view of a supply manifold for use with a gas enhanced electrosurgical instrument.

Referring now to FIG. 3, there is disclosed a novel fluid supply manifold 50 for use with electrosurgical instrument assembly 10. Manifold 50 provides multiple ports or docking stations for receipt of various supply canisters or sources and to meter the materials contained therein into the gas stream of electrosurgical instrument assembly 10. Manifold 50 generally includes a manifold housing 52 having one or more docking stations or connection ports, such as, for example connection ports 54, 56, 58 and 60 for receipt of various fluid supply sources. Some of the fluid supply sources that may be provided to manifold 50 include wound mediating substances, saline, and other tissue treating materials. Additionally, the source of propellant gas, such as for example, argon gas, may be provided in a pressurized canister inserted into one or more of the connection ports. Alternatively, a gas supply source may be in the form of a hose connected to one of the connection ports and supplied by a bulk supply system associated with the operating room. A discharge tube 62 is provided on manifold 50 to connect manifold 50 to electrosurgical instrument assembly 10. Discharge tube 62 provides a fluid flow conduit between manifold 50 and electrosurgical instrument assembly 10.

Figure 4:
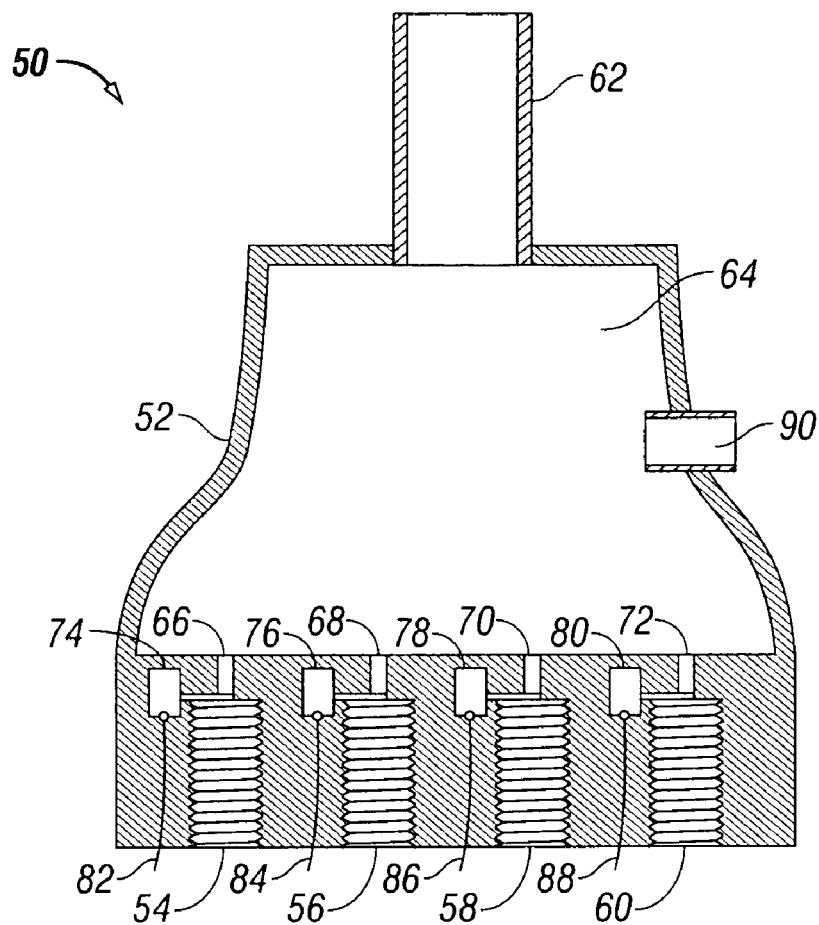
FIG. 4 is a top view, shown in section, of the supply manifold.

As best shown in FIG. 4, manifold 50 defines a mixing chamber 64 to allow the fluids contained within the various fluid supply sources to be combined and to be passed into the gas stream associated with electrosurgical instrument assembly 10. Each of connection ports 54, 56, 58 and 60 are provided with respective flow ports 66, 68, 70 and 72, respectively, which are in fluid flow communication with mixing chamber 64. Control valves 74, 76, 78 and 80 are provided at each of flow ports 66, 68, 70 and 72, respectively, to control or meter the flow of fluids from the fluid supply sources into mixing chamber 64. Individual control wires 82, 84, 86 in 88 are associated with control valves 74, 76, 78 and 80, respectively, and are connected to actuator 44 (FIG. 2). As noted hereinabove, actuator 44 may be provided with one or more control pedals 48a, 48b to operate the various control valves of manifold 50.

In one particular embodiment, manifold 50 is provided with a gas inlet 90 for receipt of a pressurized source of gas. Gas flowing through gas inlet 90 will assist in atomizing any liquid supplied by the various supply sources affixed to connection ports 54, 56, 58 and 60. As shown, by orienting gas inlet 90 at a substantially 90° angle to flow ports 66, 68, 70 and 72, the flow of pressurized gas through gas inlet 90 creates a Venturi effect to assist in drawing the fluids out of various non-pressurized supply sources and atomize the fluids within the gas stream.

Figure 5:
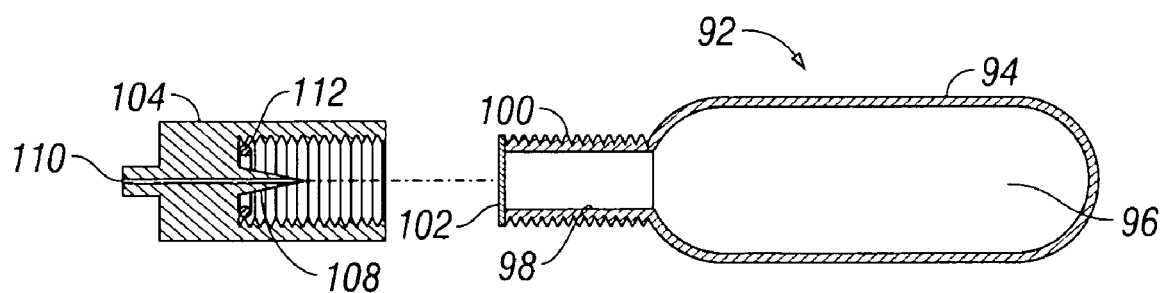
FIG. 5 is a side sectional view of one embodiment of a method of attaching a supply cylinder to the supply manifold.

Referring to FIG. 5, there is disclosed one method of connecting a supply canister, such as, for example supply canister 92 to a connection port in manifold 50. Supply canister 92 generally includes a canister body 94 defining a fluid chamber 96 therein. As noted hereinabove, supply canister 92 is provided to contain various treatment fluids such as gasses and/or pressurized or unpressurized liquids. Supply canister 92 further includes a neck 98 extending from body 94. In this particular embodiment, neck 98 has a threaded outer surface 100 to mate with a similar threaded surface of connection port in manifold 50. A septum 102 is provided on neck 98 to contain the fluids in supply canister 92 until septum 102 is pierced by a needle, or other method, associated with a connection port in manifold 50.

In this particular embodiment, the connection port by the manifold 50 is in the form of a connection port body 104, which may be integral with manifold 50 or may be a separate part that is threaded or otherwise attached to manifold 50. Connection port body 104 includes a threaded bore 106 that is configured to mate with threaded surface 100 of supply canister 92. Connection port body 104 further includes a needle 108 for piercing septum 102 on supply canister 92. A fluid flow path 110 is provided through connection port body 104 and needle 108 to allow fluids to flow from fluid chamber 96 after septum 102 has been pierced. As noted hereinabove, various control valves are provided on manifold 50 in order to control the flow of fluids out of supply canister 92 and through fluid flow path 110. An O-ring may be provided within connection port body 104 in order to seal septum 102 within connection port body 104.

In use, neck 98 of supply canister 92 is inserted toward connector port body 104 and supply canister 92 is rotated such that threaded surface 100 matingly engages with threaded bore 106 of connector port body 104. Supply canister 92 is continued to be rotated until needle 108 pierces septum 102 and septum 102 engages O-ring 112 to seal supply canister 92 within connection port 104. In this manner, a supply canister 92 is inserted into manifold 50 such that the fluids contained within fluid chamber 96 are available for supply into manifold 50 through the various control valves and thus into electrosurgical instrument 10.

Figure 6:
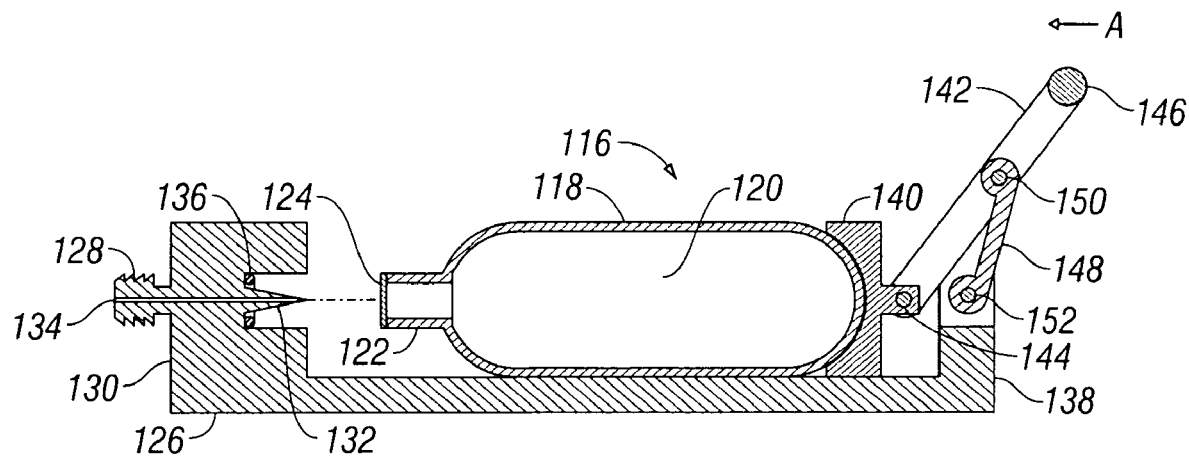
FIG. 6 is a side sectional view of an alternate embodiment of a method of attaching a supply cylinder to the supply manifold.

Referring now to FIG. 6, there is disclosed an alternate method of attaching a supply canister to a connection port, such as connection port 114, in manifold 50. In this embodiment, a supply canister 116 includes a supply body 118 defining a fluid chamber 120 similar to that disclosed hereinabove with respect to supply canister 92. However, in this embodiment, neck 122 is smooth and not threaded. Neck 122 also includes a septum 124 to retain the fluids contained within fluid chamber 120 until pierced by a needle associated with connection port 114. One method of attaching supply canister 116 to connection port 114 includes providing a generally C shaped connection port body 126 for receipt of supply canister 116. Connection port body 126 may include a ribbed connector 128 at distal end 130 of connection port body for connection to a corresponding part in manifold 50. Alternatively, ribbed connector 128 may be omitted and connection port 114 may be formed integrally with manifold 50.

Similar to connection port 104 disclosed hereinabove, connection port 114 also includes a needle 132 defining a fluid flow path 134 to transfer fluids contained within supply canister 116 to manifold 50. An O-ring 136 is provided about needle 132 to seal against septum 124 of supply canister 116. An L-shaped proximal end 138 of connection port 114 supports a driver 144 engagement with supply canister 116 in order to move supply canister 116 into engagement with needle 132. A cam bar 142 is connected to driver 140 at a pivot point 144. An opposed end of cam bar 142 from pivot point 144 defines a handle 146. In order to move cam bar 142, and thus drive driver 140 against supply canister 116, connection port 114 also includes a link 148 affixed the proximal end 138 at a pivot point 150. An opposed end of link 148 is connected to cam bar 142 at a second pivot point 152.

Figure 7:
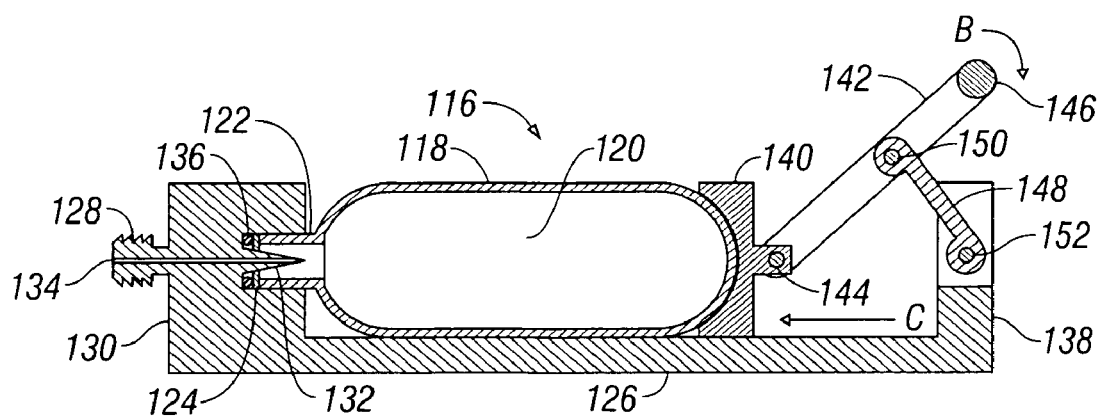
FIG. 7 is a side sectional view of the embodiment of FIG. 6 with the supply cylinder connected to the supply manifold.

Referring now to FIGS. 6 and 7, and initially to FIG. 6, in use, supply canister 116 is initially inserted in C-shaped body 126 of connection port 114. Handle 146 of cam bar 142 is moved in the direction of arrow A to move pivot point 150 to the left and over center of second pivot point 152 and thus initially engage driver 140 with body 118 of supply canister 116.

Referring now to FIG. 7, the direction of handle 146 is reversed such that handle 146 moves in the direction of arrow B to cam driver 140 in the direction of arrow C. As driver 140, and thus supply canister 116, moves in the direction of arrow C driver 140 forces neck 122 of supply canister 116 over needle 132 of connection port 114. This causes needle 132 to pierce septum 124. This motion of supply canister 116 in the direction of arrow C continues until septum 124 sealingly engages O-ring 136. At this point supply canister 116 is fully inserted within connection port 114 thereby making the fluids available within supply canister 116 to electrosurgical instrument assembly 10. While not specifically shown, in a contemplated embodiment, handle 146 of cam bar 142 can continue to be moved in the direction of arrow B such that cam bar 142 locks over link 148 in an over center fashion thereby preventing supply canister 116 from moving out of connecting port 114 due to any pressurized fluids contained within supply canister 116 or within mixing chamber 64 of manifold 50.

Referring now to FIGS. 8 and 9, the attachment of manifold 50 directly to electrosurgical instrument 10 will now be described. With initial reference to FIG. 8, in one embodiment, manifold 50 may be connected directly to proximal end 30 of electrosurgical instrument 12. This may be accomplished by inserting discharge tube 62 directly into or about flow tube 24. The propellant gas source may be connected directly to one of connection ports 54, 56, 58 or 60 as a line from a bulk source or may be provided in a supply canister as described hereinabove. Here the propellant gas will enter electrosurgical instrument 12 through mixing chamber 64 of manifold 50 and into flow tube 24 for discharge out of fluid discharge port 26. As an alternative, the propellant gas source may be connected to flow tube 24 at any point along flow tube 24 and independent of manifold 50.

Referring to FIG. 9, there is disclosed an alternative method of attaching manifold 50 to electrosurgical instrument 12. In this embodiment flow tube 24 is split in half resulting in a first flow tube half 154 having a distal end 156 adjacent fluid discharge port 26. A second flow tube half 158 has a proximal end 160 adjacent proximal end 30 electrosurgical instrument 12. Proximal end 160 may be connected to the propellant gas source. A second mixing chamber 162 is provided intermediate first flow tube half 154 and second flow tube half 158. Specifically, a distal end 164 of second flow tube half 158 enters second mixing chamber 162 while a proximal end 166 of first flow tube half 154 also enters mixing chamber 162. Mixing chamber 162 further includes an entry port 168 for receipt of discharge tube 62 of manifold 50.

In this embodiment, fluids provided by various supply canisters attached to connection ports 54, 56, 58, and 60 are initially mixed within mixing chamber 64 of manifold 50. As the propellant gas is forced through flow tube 24, the propellant gas moves and mixes with the combination of fluids mixed within mixing chamber 64, as they pass through discharge tube 62 and into second mixing chamber 162.

Figure 10:
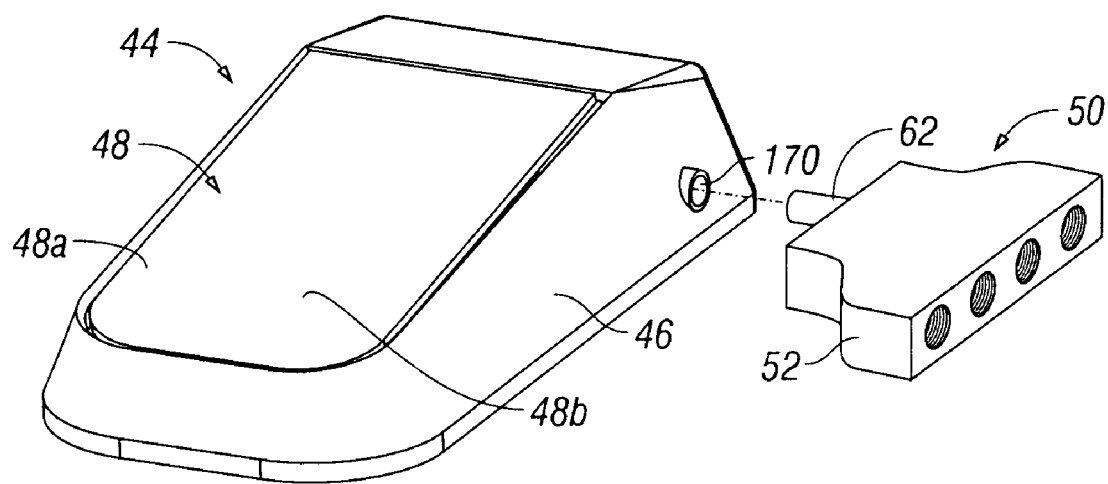
FIG. 10 is a perspective view of an actuator and supply manifold prior to attachment.
Figure 11:
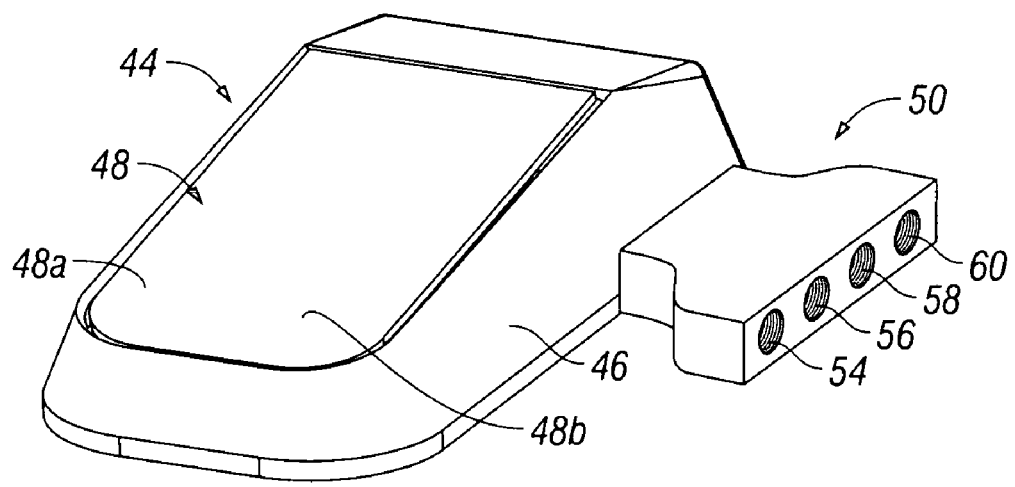
FIG. 11 is a perspective view of the embodiment of FIG. 10 with the supply manifold attached to the actuator.

Referring now to FIGS. 10 and 11, there is disclosed a method of attaching manifold 50 directly to actuator assembly 16. This may be useful where it is desirable to premix the various fluids provided by the various supply canisters with the gas propellant source prior to the entry of the gas propellant source into electrosurgical instrument 12. Referring initially to FIG. 10, as noted above, actuator assembly 16 includes foot operated actuator 44 having a foot switch 48 which may include one or more control pedals, such as, pedals 48a and 48b. In this embodiment, housing 46 of foot operated actuator 44 includes an actuator side port 170 for receipt of discharge tube 62 of manifold 50.

Referring now to FIGS. 10 and 11, in use, discharge tube 62 of manifold 50 is inserted into and secured within actuator side port 170 of foot operated actuator 44. As shown in FIG. 11, once manifold 50 has been connected to foot operated actuator 44, pedals 48a and 48b may be manipulated to initiate the flow of the gas propellant source to electrosurgical instrument 12. Manipulation of pedals 48a and 48b also controls the flow of liquids contained within the various supply canisters, by means of the control valves 74, 76, 78 and 80 (FIG. 4) associated with connection ports 54, 56, 58 and 60 as described hereinabove, to electrosurgical instrument 12. Various supply canisters may be connected to manifold 50 prior to or after connection of manifold 50 with foot operated actuator 44. Additionally, the gas propellant source may be attached directly to foot operated actuator 44 or may be routed through one of connection ports 54, 56, 58 or 60.

Figure 12:
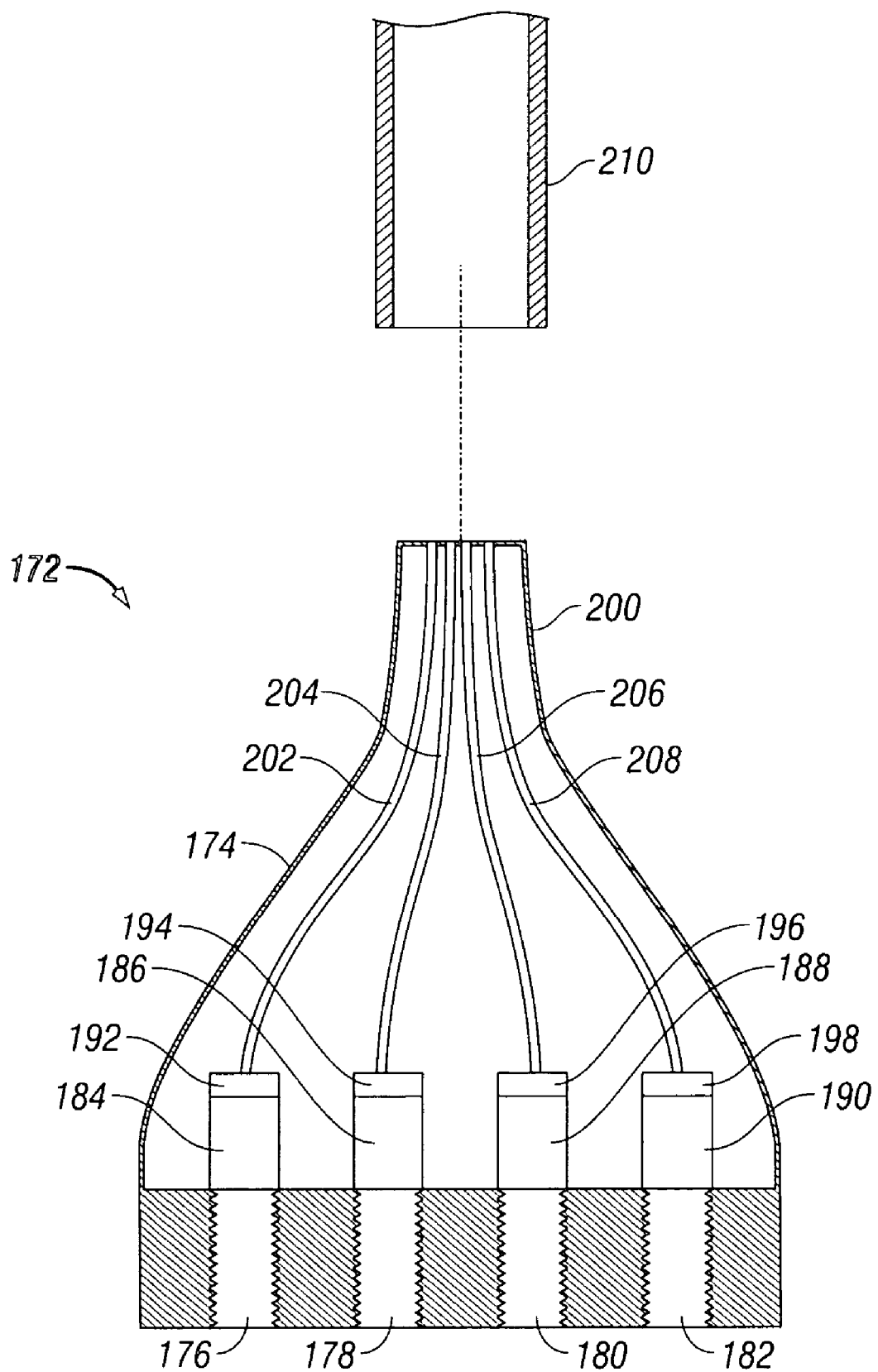
FIG. 12 is a top view, shown in section, of an alternate embodiment of a supply manifold.

Referring now to FIG. 12, there is disclosed an alternative embodiment of a supply manifold for use with a gas enhanced surgical instrument. Unlike manifold 50 described hereinabove manifold 172 does not include a mixing chamber, but rather provides individual flow lines from the various connection ports directly into the electrosurgical instrument for mixing within a fluid flow line or separate mixing chamber associated with the electrosurgical instrument. Manifold 172 generally includes a housing 174 having connection ports 176, 178, 180 and 182 for receipt of various fluid supply sources. As with manifold 50, connection ports 176, 178, 180 and 182 include respective flow ports 184, 186, 188 and 190. Control valves 192, 194, 196 and 198 are provided to control the flow of fluids from various supply canisters to the electrosurgical instrument.

Housing 174 of manifold 172 includes a tapered neck 200 to channel individual supply tubes 202, 204, 206 and 208, from respective control valves 192, 194, 196 and 198, through neck 200 to an electrosurgical instrument. As shown, neck 200 is configured to mate with an electrosurgical instrument assembly port 210 of an associated electrosurgical instrument assembly.

Figure 13:
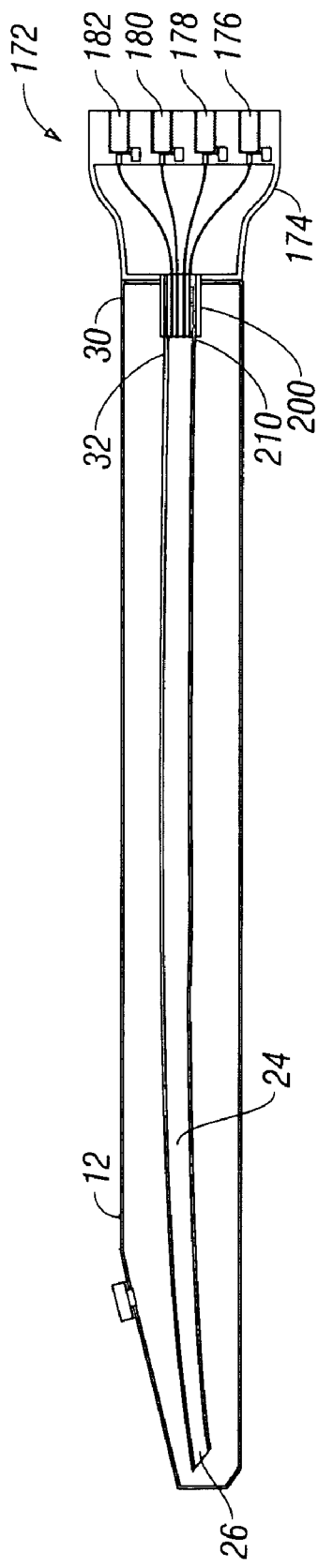
FIG. 13 is a side view, partially shown in section, of one embodiment of a gas enhanced electrosurgical instrument with the supply manifold of FIG. 12 mounted thereon.
Figure 14:
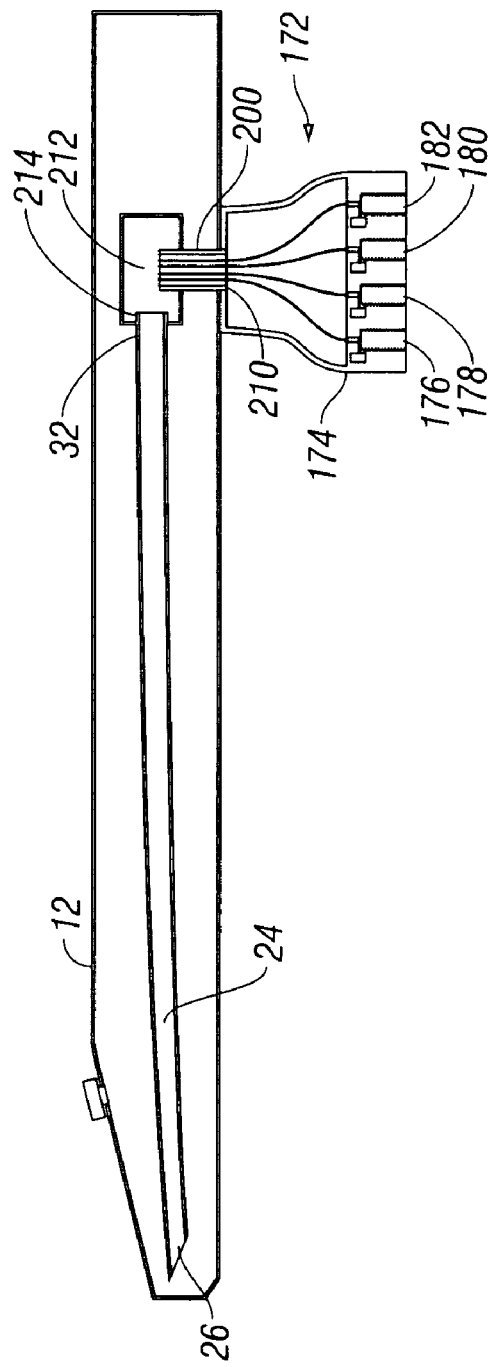
FIG. 14 is a side view, partially shown in section, of an alternate embodiment of a gas enhanced electrosurgical instrument with the supply manifold of FIG. 12 mounted thereon.

Referring now to FIGS. 13-15, various methods of affixing manifold 172 to an electrosurgical instrument, such as electrosurgical instrument 12 will now be described. Referring initially to FIG. 13, manifold 172 is affixed to a proximal end 30 of electrosurgical instrument 12. This is accomplished by inserting tapered neck 200 of housing 174 into electrosurgical instrument assembly port 210 located at proximal end 30 electrosurgical instrument 12 such that the various supply tubes are in fluid communication with proximal end 32 of flow tube 24. Alternatively, tapered neck 200 may be positioned over electrosurgical instrument assembly port 210. In this configuration, an independent source of gas propellant is not provided directly to electrosurgical instrument 12. Rather, however, one of connection ports 176, 178, 180 or 182 is used to connect to an external source of propellant gas, such as, for example, argon gas provided either in bulk or in a fluid supply canister. The remaining connection ports, as with prior embodiments, are unavailable for receipt of fluid canisters containing various tissue treatment fluids, such as, for example, wounded mediating substances.

Electrosurgical instrument 12 is used in known fashion to cauterize or otherwise treat tissue in known fashion. The various fluids provided by various supply canisters are mixed with the propellant gas within flow tube 24. The propellant gas also serves as an ionizing agent as well as a propellant for fluids provided through the remaining connection ports.

Referring now to FIG. 14, there is disclosed an alternate method of affixing manifold 172 to electrosurgical instrument 12. In this embodiment, a mixing chamber 212 is provided at a proximal end 32 of flow tube 24. Proximal end 32 enters a flow tube port 214 of mixing chamber 212 to allow mixing chamber 212 to be in fluid communication with flow tube 24. Mixing chamber 212 includes electrosurgical instrument port 210 for receipt of tapered neck 200 of manifold 172. In this embodiment, fluids provided by the various supply canisters enter into mixing chamber 212 and are combined therein with the propellant fluid gas. Electrosurgical instrument 12 is then used in known fashion to cauterize or otherwise treat tissue.

Referring now to FIG. 15, there is disclosed a further alternate method of affixing manifold 172 to electrosurgical instrument 12. This embodiment is substantially similar to that disclosed in FIG. 14, however, mixing chamber 212 is positioned more distally within electrosurgical instrument 12 to position mixing chamber 212 closer to discharge port 26. This may be advisable in some instances where the various substances do not remain in mixed suspension for relatively long periods of time.

Various modifications may be made to the embodiments disclosed herein. For example, more or less than the disclose connection ports may be provided for receipt of various fluid supply canisters. Further, the disclose manifolds may be affixed to the electrosurgical instrument assembly at locations other than the actuator or electrosurgical instrument itself. Additionally, the disclose manifolds may be utilized with other surgical instruments other than the disclosed electrosurgical instrument to provide a combination of fluid medicines to tissue during the surgical operations. Therefore, the above description should not be construed as limiting, but merely as exemplifications of particular embodiments. Those skilled in the art will envision other modifications within the scope and spirit of the claims appended hereto.

The invention claimed is:

1. A surgical instrument assembly comprising:
   a surgical instrument including a housing having a fluid flow tube, the fluid flow tube having a discharge port defined at a distal end of the housing;
   an actuator assembly having an actuator that controls the flow of fluid through the fluid flow tube; and
   a manifold operably coupled to the housing and configured for operable engagement with at least a first source of pressurized gas and one or more sources of fluid, the at least first source of pressurized gas and one or more sources of fluid being arranged such that releasing the pressurized gas from the source of pressurized gas draws one or more fluids from the one or more sources of fluid.

2. The surgical instrument assembly as recited in claim 1, wherein the manifold is attached to the actuator of the actuator assembly.

3. The surgical instrument assembly as recited in claim 1, wherein the manifold is attached to a proximal end of the housing.

4. The surgical instrument assembly as recited in claim 1, wherein the manifold is attached to a mixing chamber on the surgical instrument.

5. The surgical instrument assembly as recited in claim 1, wherein the manifold is configured to dispense fluid from at least three sources.

6. The surgical instrument assembly as recited in claim 1, wherein the actuator assembly is located remotely from the housing.

7. The surgical instrument assembly as recited in claim 1, wherein the at least first source of pressurized gas is maintained within the actuator assembly.

8. The surgical instrument assembly as recited in claim 1, wherein the one or more fluids are drawn from the one or more sources of fluids by the Venturi effect created with the manifold.

9. A gas enhanced electrosurgical instrument assembly comprising:
   an electrosurgical instrument having a fluid flow tube, the fluid flow tube having a discharge port defined at a distal end of the surgical instrument;
   a generator that provides a source of energy to the electrosurgical instrument;
   a manifold configured for operable engagement with at least a first source of pressurized gas and one or more sources of fluids, the at least first source of pressurized gas and one or more sources of fluid being arranged such that releasing the pressurized gas from the source of pressurized gas draws one or more fluids from the one or more sources of fluid; and
   an actuator assembly having an actuator that controls the source of energy provided by the generator and the flow of fluids from the manifold to the fluid flow tube of the electrosurgical instrument, wherein the manifold is operably coupled to the actuator assembly.

10. A surgical instrument assembly comprising:
    a surgical instrument including a housing having a fluid flow tube, the fluid flow tube having a discharge port defined at a distal end of the housing;
    an actuator assembly having an actuator that controls the flow of fluid through the fluid flow tube; and
    a manifold configured for operable engagement with at least a first source of pressurized gas and one or more sources of fluid, the at least first source of pressurized gas and one or more sources of fluid being arranged such that releasing the pressurized gas from the source of pressurized gas draws one or more fluids from the one or more sources of fluid, wherein the actuator assembly is located remotely from the housing.

11. A surgical instrument assembly comprising:
    a surgical instrument including a housing having a fluid flow tube, the fluid flow tube having a discharge port defined at a distal end of the housing;
    an actuator assembly having an actuator that controls the flow of fluid through the fluid flow tube; and
    a manifold configured for operable engagement with at least a first source of pressurized gas and one or more sources of fluid, the at least first source of pressurized gas and one or more sources of fluid being arranged such that releasing the pressurized gas from the source of pressurized gas draws one or more fluids from the one or more sources of fluid, wherein the at least first source of pressurized gas is maintained within the actuator assembly.

12. A surgical instrument assembly comprising:
    a surgical instrument including a housing having a fluid flow tube, the fluid flow tube having a discharge port defined at a distal end of the housing;
    an actuator assembly having an actuator that controls the flow of fluid through the fluid flow tube; and
    a manifold configured for operable engagement with at least a first source of pressurized gas and one or more sources of fluid, the at least first source of pressurized gas and one or more sources of fluid being arranged such that releasing the pressurized gas from the source of pressurized gas draws one or more fluids from the one or more sources of fluid, wherein the one or more fluids are drawn from the one or more sources of fluids by the Venturi effect created with the manifold.

* * * * *